United States Patent [19]

Zowtiak et al.

[11] Patent Number: 4,960,708

[45] Date of Patent: Oct. 2, 1990

[54] PRESSURIZED PACKAGED REFERENCE LIQUID FOR BLOOD GAS ANALYSIS

[75] Inventors: John M. Zowtiak; Bruce I. Mayall, both of Mission Viejo, Calif.

[73] Assignee: Baxter International Inc., Deerfield, Ill.

[21] Appl. No.: 257,017

[22] Filed: Oct. 13, 1988

[51] Int. Cl.$^5$ .............................. G01N 31/00
[52] U.S. Cl. .................. 436/11; 252/408.1; 436/8
[58] Field of Search ................... 436/8–19; 252/408.1; 73/1 R, 1 G

[56] References Cited

U.S. PATENT DOCUMENTS

| | | | |
|---|---|---|---|
| 2,160,367 | 11/1937 | Maxfield | 93/3 |
| 3,466,249 | 7/1969 | Anderson | 252/408 |
| 3,681,255 | 9/1972 | Wilfore | 252/408 |
| 3,973,913 | 7/1976 | Louderback et al. | 23/230 B |
| 4,001,142 | 10/1977 | Turner | 252/408 |
| 4,116,336 | 4/1978 | Sorensen et al. | 206/524.8 |
| 4,151,108 | 6/1979 | Sorensen et al. | 252/408 |
| 4,163,734 | 4/1979 | Sorensen et al. | 252/408 |
| 4,199,471 | 1/1980 | Louderback et al. | 252/408 |
| 4,279,775 | 7/1981 | Louderback et al. | 252/408 |
| 4,289,648 | 6/1981 | Hoskins et al. | 252/408 |
| 4,299,728 | 12/1981 | Cormier et al. | 252/408 |
| 4,365,715 | 6/1982 | Egli | 206/524.8 |
| 4,369,127 | 5/1983 | Cormier et al. | 436/111 |
| 4,458,021 | 1/1984 | Herring | 436/11 |
| 4,469,792 | 7/1984 | Simmons et al. | 436/11 |
| 4,470,520 | 11/1984 | Sullivan | 222/94 |
| 4,600,697 | 7/1986 | Smernoff | 436/11 |
| 4,722,904 | 12/1988 | Feil | 436/11 |

Primary Examiner—Christine M. Nucker
Assistant Examiner—T. J. Wallen
Attorney, Agent, or Firm—Bernard, Rothwell & Brown

[57] ABSTRACT

A packaged single-phase reference liquid comprising a gas and liquid-impermeable sealed container and a reference liquid containing a highly diffusible gas.

13 Claims, No Drawings

PRESSURIZED PACKAGED REFERENCE LIQUID FOR BLOOD GAS ANALYSIS

BACKGROUND OF THE INVENTION

This invention relates to a packaged reference liquid for calibration of blood gas-measuring equipment.

In the field of diagnostic medicine, the determinations of the partial pressures of carbon dioxide ($PCO_2$) and oxygen ($PO_2$) in the blood are clinically important. These measurements are an indication of respiratory efficiency, renal function, efficacy of inhalation therapy and the like.

The clinical laboratory has available to it a variety of instruments for conducting or performing these measurements. Typically these instruments require periodic calibration with standards or reference liquids.

The use of a reference standard for calibrating or checking the accuracy of a measuring device is well-known. However, calibration of equipment designed to measure blood gases, such as carbon dioxide and oxygen, presents special problems. In the past, reference materials were not readily available and had to be prepared by the medical technologist immediately prior to performing the subject test. Generally, these materials were prepared by adding a gas mixture with known fractions of oxygen and carbon dioxide gases to a tonometer containing a control fluid sample at a buffered pH value. The gas and liquid phases were allowed to equilibrate within the tonometer, and an aliquot thereafter removed by the technician for use as a control for the blood gas instrumentation. Prior to the development of commercially available reference liquids, blood gas analyses could only be performed by trained technicians in specially equipped laboratories. Even when such reference liquids were available, they had a limited shelf life and would readily undergo changes in the dissolved gas concentrations upon exposure to the atmosphere.

Recently, packaged controls have become commercially available for blood gas testing. Such controls are provided in sealed containers, and do not have to be synthesized by a technician. Pre-packaged controls may be in the form of either single-phase (liquid) or two-phase (gas-liquid) products. A two-phase control generally requires equilibration at a constant temperature prior to use. Single phase reference liquids avoid the need for this equilibration, and thus are more convenient for the user.

U.S. Pat. No. 3,681,255 discloses the use of flexible, gas-tight containers containing a single-phase reference liquid. The liquid is prepared and packaged at ambient barometric pressures. These products suffer from a disadvantage, in that, under certain storage and transportation conditions, they may become unreliable. For example, air freight transportation conditions could easily involve situations where the external pressure would be so low that microbubbles would be formed in a liquid saturated with gases at standard atmospheric pressure.

In the system described in U.S. Pat. No. 4,116,336, there is an attempt to overcome the problem of microbubble formation. This system employs a subatmospheric pressure on the reference liquid at the time of preparation, filling and sealing. Thus, the total gas and vapor pressures in the liquid are below 600 mm Hg. Under most conditions, this system will not undergo phase separation. Preparation of these products is cumbersome, requiring extensive monitoring and pressure-controlling equipment and personnel. Additionally, microbubble formation, with the aforementioned untoward effects, could still occur should the packaged product be exposed to external pressures below 600 mm Hg.

U.S. Pat. No. 4,470,520 discloses a blood-gas quality control reagent, in a single liquid phase, stored in a gas impermeable tube with a valve attached for the release of the control into a blood-gas analyzer. This first tube is enclosed by a second gas-impermeable container, with the space between the two containers filled with compressed gas. This product is expensive and requires specialized manufacturing equipment. Additionally, it is not designed to be used with analyzers which have a sensor attached to an arterial line.

A need exists for a gas-equilibrated reference liquid that is convenient to prepare, affords the end user the assurance of a single-phase liquid reference regardless of transport, storage, or use conditions, and that may be safely used in an analyzer with a sensor attached to an arterial line.

SUMMARY OF THE INVENTION

In accordance with the present invention, a packaged reference liquid comprises: (a) a sealed, flexible, gas and liquid-impermeable container; and (b) an aqueous solution contained in said container without any separate gas phase. The solution contains a known concentration of oxygen or carbon dioxide or both, wherein the sum of the partial pressures of oxygen and carbon dioxide is less than about 350 mm Hg (at 37° C.). The solution further contains a highly diffusible gas at a concentration such that the total of all gas and vapor pressures is from about 550 to about 800 mm Hg (at 37° C.). As used hereinafter, unless otherwise indicated, the term "total gas pressure" shall mean the sum of all gas partial pressures and the vapor pressures of all species contained in the reference liquid. The container is pressurized to provide a total hydraulic pressure within the container which is greater than the total gas pressures, and which is sufficient to prevent a phase separation during conditions of storage and transportation. This invention provides a reliable reference liquid regardless of the barometric pressure conditions during transport or storage. It has the advantage of ease of preparation, since it does not require extensive pressure-monitoring and control equipment. It has the further advantage of safety to patients, when used to calibrate a blood-gas instrument having a sensor attached to an arterial line.

DETAILED DESCRIPTION OF THE INVENTION

The present invention provides a positively pressurized package containing a reference liquid which may be used for quality control, including the calibration or checking of blood gas-measuring instruments. The reference liquid has known concentrations of oxygen or carbon dioxide or both and may optionally be buffered to a known pH. The reference liquid further contains a highly diffusible gas and is enclosed in a gas- and liquid-tight container, without the presence of a separate gas phase. The container is sealed and pressurized such that the hydraulic pressure in the container is greater than the total gas pressure of the reference liquid and is sufficient to prevent phase separation during transport and storage of the reference liquid.

The reference liquid advantageously is a water-based system, such as a solution, an emulsion, a colloidal suspension or the like. For reference liquids that may be used for calibrating gas sensors in arterial blood lines, the solution preferably is a physiologically compatible, buffered isotonic saline solution having a pH from about 6 to about 7. For such uses, the solution most preferably is buffered to a physiologically safe pH.

The sum of the partial pressures of the oxygen and carbon dioxide in the reference liquid is generally less than about 350 mm Hg. Unless stated otherwise, the partial pressures referred to herein are those pressures which would be exhibited when measured at 37° C. Those skilled in the art will recognize that gas partial pressures and liquid and solid vapor pressures may vary if measured at a different temperature. In preferred embodiments, the concentration of oxygen in the reference liquid is such that the $PO_2$ ranges from about 0 to about 300 mm Hg, most preferably from about 60 to about 150 mm Hg. Preferred reference liquids contain both carbon dioxide and oxygen, and in such liquids, the concentration of carbon dioxide is such that the $PCO_2$ ranges from about 40 to about 80 mm Hg.

The reference liquid further contains a highly diffusible gas. By "highly diffusible" is meant a gas which readily diffuses (e.g., within a few minutes or less) through such materials as plastic tubing and fittings, aqueous solutions and natural tissues, such as blood vessels. Hydrogen and helium are preferred highly diffusible gases. Because of the flammability of hydrogen, helium is preferred. The partial pressure of the highly diffusible gas is controlled such that the total gas pressure in the reference liquid generally ranges from about 550 mm Hg to about 800 mm Hg, most preferably from about 760 mm Hg to about 800 mm Hg.

The reference liquid is contained in a liquid- and gas-impermeable sealed container having at least one movable boundary. In one embodiment at least a portion of the walls of the container are flexible and exhibit some degree of elasticity. This flexibility and elasticity prevent rupture of the container upon thermal expansion of the reference liquid and also facilitate pressurization of the fluid contents of the container by application of an external force on the container. The container may take any of a variety of forms. For example, the container may be a plastic bag constructed of liquid- and gas-impermeable material. In a preferred embodiment, the container is a metal tube of aluminum, tin or other appropriate gas-impermeable metal which possesses the requisite physical characteristics, including flexibility and elasticity. If a metal is used, it is preferably not reactive with the reference liquid or its components or alternatively, may be lined with a relatively inert material. Alternatively, the container may be a laminate or co-extruded bag wherein one or more of the layers is substantially impermeable to gas and liquid transmission. Examples of such impermeable layers include metal layers, such as aluminum (either foil or vapor deposited), polyvinylidine chloride (Saran ® or Saran HB ®) or polyacrylonitrile (Barex ®) Another type of container that may be employed is a syringe with a movable plunger biased against the reference liquid.

The hydraulic pressure of the reference liquid is higher than the total gas pressure within the liquid. Such pressure is high enough to prevent a gas phase separation upon exposure of the packaged reference liquid to conditions that will be encountered during storage and transport. In general, the pressure will prevent a phase separation at the highest temperatures and altitudes to be encountered. Preferably, the hydraulic pressure ranges from about 200 to about 1,000 mm Hg, most preferably from about 300 to about 800 mm Hg. This elevated pressure may conveniently be achieved by slightly pressurizing the reference liquid container during the packaging and sealing operations. In the case of a metal or plastic tube, such pressurization can be accomplished by placing an extra crimp in the closing, such that a slightly elevated pressure is created. The packaged reference liquid of this invention provides a convenient and stable product. The elevated fluid pressure within the package prevents any phase separation in all normal modes of transportation, storage and use. Thus, the products may be used at high altitude locations or transported by aircraft without concern about phase separation.

A drawback to pressurized solutions in the past has been that, upon opening, microbubbles can rapidly form in the solution. The formation of microbubbles can drastically alter the gas composition and render the solution useless as a reference liquid. Moreover, in the case of reference liquids used to calibrate gas sensors in arterial blood lines, such microbubbles can be hazardous to the patient. The present invention overcomes the risk of microbubbles in that, when the reference liquid container is opened for use, the highly diffusible gas rapidly diffuses out of the solution through the sensor or associated plastic tubing or fittings. Such diffusion leaves the reference liquid solution sub-saturated and thus incapable of nucleating bubbles.

The packaged reference liquids of this invention are also advantageous because of their ease of preparation. By employing a highly diffusible gas, such as hydrogen or helium, the need for sophisticated pressure control during the preparation and filling is eliminated. The solutions may conveniently be prepared at standard atmospheric pressure using a mixture of the reference gas (i.e., oxygen and/or carbon dioxide) and the highly diffusible gas. The highly diffusible gas ensures that microbubbles do not form when the reference liquid is transferred to a conventional blood gas analysis instrument, especially if the sensors are in an arterial blood line. The highly diffusible gas diffuses so easily and rapidly that it escapes through plastic tubing and sensor walls without forming gas bubbles, even if the internal pressure of the tubing is lower than that of the package pressure of the reference liquid. Because the reference gases are substantially less diffusible than the highly diffusible gas, their concentrations remain stable for at least the time required to calibrate the instrument. Thus, while the highly diffusible gas may leave the system after opening of the package and transfer of the contents to a gas analysis instrument, the reference solution remains a single phase and the concentrations of the reference gases remain constant. It should be noted that the reference liquids of this invention are specifically designed for gas-measuring equipment which employs tubing, fittings, sensors and the like which are permeable to the highly diffusible gas.

The invention is further illustrated by the following example, which is not intended to be limiting.

EXAMPLE

An isotonic saline solution, having the osmolality of human blood serum is prepared by adding 9 g sodium chloride per liter to achieve a concentration of 0.9%

W:V. It is buffered by the addition of tris(hydroxymethyl)aminomethane. The pH is adjusted by the addition of hydrochloric acid to obtain a pH value of approximately 7.5. This solution is placed in an equilibration tank with a thermostatic control. The thermostat is set at 37° C., and equilibration with a gas mixture is begun at 760 mm Hg barometric pressure. The contents of the gas mixture are 14% $O_2$, 7% $CO_2$, balance He. Subsequent to equilibration, which occurs after 5-30 minutes, depending on a method of equilibration, the reference liquid is transferred to a gas-tight container which has been flushed with the equilibrating gas mixture. This container, with no gas-phase present, is sealed by crimping. A positive internal pressure is then applied by additional crimping or by a separate, spring-loaded device. The resulting package will provide accurate calibration, even upon travel through space, for blood gas analyzers. It will show the following data at 37° C.:100 mm HG ($PO_2$), 50 mm Hg ($PCO_2$), 7.38 (pH).

We claim:

1. A packaged single-phase reference liquid, which comprises:
   (a) a sealed, flexible, gas- and liquid-impermeable container, and
   (b) an aqueous solution contained in said container without any gas phase, said solution containing a known concentration of oxygen or carbon dioxide or both, wherein the sum of the partial pressures of oxygen and carbon dioxide are less than about 350 mm Hg (at 37° C.), said solution further containing a highly diffusible gas at a concentration such that the total gas pressure is from about 550 to about 800 mm Hg (at 37° C.), and wherein the total hydraulic pressure within the container is greater than the total gas pressure and is sufficient to prevent a gas phase separation during conditions of storage and use.

2. The packaged reference liquid of claim 1, wherein the aqueous solution contains dissolved oxygen and carbon dioxide, the partial pressure of oxygen being from about 0 mm Hg to about 300 mm Hg (37° C.) and the partial pressure of carbon dioxide being from about 20 to about 100 mm Hg (at 37° C.).

3. The packaged reference liquid of claim 1, wherein the total of all gas partial pressures is from about 700 to about 800 mm Hg (at 37° C.).

4. The packaged reference liquid of claim 1 or 2, wherein the highly diffusible gas is hydrogen or helium.

5. The packaged reference liquid of claim 4, wherein the highly diffusible gas is helium.

6. The reference liquid of claim 1, wherein the aqueous solution is buffered to a known pH.

7. The reference liquid of claim 6, wherein said pH is from about 6.5 to about 7.5.

8. The packaged reference liquid of claim 1, wherein said aqueous solution is pH-buffered isotonic normal saline having substantially the same osmolality as human blood serum.

9. The packaged reference liquid of claim 1, wherein the container is a bag.

10. The packaged reference liquid of claim 9, wherein said bag is constructed from a laminate having at least one layer impermeable to gas-liquid transmission.

11. The packaged reference liquid of claim 10, wherein said impermeable layer is a metal layer.

12. The packaged reference liquid of claim 1, wherein the container is a metal tube.

13. The packaged reference liquid of claim 1, wherein the container is a syringe having a movable plunger biased against the reference liquid.

* * * * *